US00PP10682P

United States Patent [19]

Plate

[11] Patent Number: Plant 10,682

[45] Date of Patent: Nov. 10, 1998

[54] PHALAENOPIS ORCHID PLANT NAMED 'NOPSYA'

[75] Inventor: Renate Plate, Bremen, Germany

[73] Assignee: Wolfgang Bock Pflanzenexport KG, Bremen, Germany

[21] Appl. No.: 848,186

[22] Filed: Apr. 29, 1997

[51] Int. Cl.[6] ..... A01H 5/00

[52] U.S. Cl. ..... Plt./87.3

[58] Field of Search ..... Plt./87.3

*Primary Examiner*—James R. Feyrer

*Attorney, Agent, or Firm*—Foley & Lardner

[57] ABSTRACT

A new and distinct Phalaenopsis orchid plant named 'Nopsya', particularly characterized by its attractive pink striped flowers with a dark center, economical propagation via tissue culture, very rapid growth, long lasting flowers, and plant dimensions suitable for packaging and shipping to market.

2 Drawing Sheets

The present invention comprises a new and distinct cultivar of Phalaenopsis, a genus in the family Orchidaceae, referred to by the cultivar name 'Nopsya'. The new cultivar is a hybrid selected from the progeny of a cross of plants identified below.

Phalaenopsis comprise a genus of about 55 species of herbaceous perennials many of which, or the hybrids thereof, are suitable for cultivation in the home or greenhouse. Phalaenopsis are predominantly epiphytic or rock-dwelling, and are native to tropical Asia, Malay, Archipelago, and Oceania. The species typically have 2-ranked fleshy oblong or elliptic leaves affixed to a short central stem (monopodial growth), which vary in size from 5 to 8 inches to over 2 feet. The leaves may be entirely green or mottled with silver grey.

Phalaenopsis orchids, often referred to as "Moth Orchids" in the horticultural trade, are frequently used to furnish cut flowers for the florist trade, or are sold as flowering potted plants for home or interiorscape.

Phalaenopsis produce upright or pendent lateral racemes, often with many showy flowers which open in succession beginning with the lowermost. The flowers possess three sepals, and three petals, the lateral ones being alike. The lowermost petal, called the labellum, is three lobed and is often more brightly colored than the other flower segments. Flower colors include various shades of pink, white, yellow, and red-brown.

Phalaenopsis orchids are typically propagated from seeds. Asexual propagation of Phalaenopsis is often done from off-shoots which frequently arise from the lower bracts of the inflorescence. The resulting plants are detached from the mother plant and may be planted in a suitable substrate. Asexual propagation of Phalaenopsis through the use of tissue culture, though feasible, is not widely practiced because it is often relatively inefficient and costly as currently applied.

The new cultivar is a product of a breeding program carried out by the inventor Renate Plate in Bremen, Germany. The new cultivar 'Nopsya' is a result of a cross of selected, but unnamed parentage made in Bremen, Germany in 1984 by the inventor. The new cultivar 'Nopsya' was discovered from the progeny of the stated cross in Bremen, Germany by the inventor Renate Plate on (Sep. 3, 1986.

Asexual propagation by tissue culture done under the supervision of the inventor in Bremen, Germany was used to increase the number of plants for evaluation and has demonstrated the stability of the combination of characteristics from generation to generation.

The following observations, measurements and values describe plants grown in Lake Worth, Fla. under greenhouse conditions which closely approximate those generally used in horticulture practice.

The following traits have been repeatedly observed to be characteristics which in combination distinguish 'Nopsya' from generally available seedling-derived Phalaenopsis common in commercial cultivation.

1. The flowers produced by 'Nopsya' are light pink with fine pink stripes and a contrasting dark purple center.

2. The flowers produced by plants of 'Nopsya'have good substance and are long lasting.

1 3. The inflorescence produced by plants of 'Nopsya' is short and easily staked and packaged for shipping.

4. Plants of 'Nopsya' grow very quickly, producing marketable flowering plants in approximately 9–11 months.

5. Plants of 'Nopsya' may be propagated economically and uniformly using tissue culture.

Perhaps the closest commercial comparison can be made to seedling-derived Phalaenopsis which are heterogeneous genetically, and typically lack uniformity in growth vigor, habit, and flower quality. Because the reference point has inconsistent characteristics, a direct comparison for 'Nopsya' is not available. 'Nopsya' is a single genotype and asexually propagated via tissue culture. Thus, its combined horticultural properties listed above are uniform and predictable.

All color references are measured against The Royal Horticultural Society Colour Chart. Colors are approximate as color depends on horticultural practices such as light level and fertilization rate, among others, without, however any change in genotype.

In the color photographic drawings, the photo on Sheet 1 comprises a top perspective view of the inflorescence and foliage of a group of plants of 'Nopsya' in 10.2 cm pots. The photograph was taken approximately 12 months after planting a 16 week old liner obtained by tissue culture and grown under appropriate growing conditions.

The photo on Sheet 2 is an enlarged view showing 2 flowers in much greater detail Colors are as accurate as possible with color illustrations of this type.

Origin: Seedling from a cross of selected, but unnamed parentage.

Classification: *Phalaenopsis hybrid* cv. 'Nopsya'.

Propagation: Asexual propagation by tissue culture.

Inflorescence:

*Description of flowers.*—The sepals and petals are white or light pink with fine light pink stripes along the veins. The lateral petals are also centrally flushed with light pink. The lateral (lower) sepals are suffused with minute dark pink speckles near their base. The sepals are elliptic-ovate in shape, and the lateral petals are broadly ovate with a rounded apex. The sepals and petals are slightly cupped. The labellum is deeply three-lobed with two prominent callosities at the central junction of the lateral lobes and base of the midlobe. The lateral lobes of the labellum fold upward about the column. The midlobe extends forward and is terminated by two twisted filiform appendages at the apex. The lateral lobes of the labellum are obovate in shape, the midlobe is triangular. The labellum is dark pink with a white center which is spotted and striped with dark pink. The two callosities are yellow with minute dark pink spots.

*Dimensions.*—Overall: Approximately 8.0 cm to 8.6 cm wide, and 7.1 to 7.8 in height. Sepals: Approximately 3.8 cm to 4.1 cm long, and 2.3 cm to 2.5 cm wide. Petals: Approximately 4.0 cm to 4.2 cm long, and 4.5 cm to 4.7 cm wide. Labellum: Approximately 2.9 cm to 3.1 cm long, and 2.2 cm wide (not flattened). Raceme: Dimensions: The raceme is typically staked upright to a height of approximately 37 cm. The raceme is approximately 55 cm from base to tip, and 0.5 cm in diameter at its midpoint. The raceme is 200 A, 187 A in color.

*Flower color.*—Sepals: Adaxial surface: Lighter than but closest to 76 D, with 87 A stripes, and 60 C speckles. Abaxial surface: 69 B, with 87 B stripes. Lateral Petals: Adaxial surface: Lighter than, but closest to 76 D, flushed with 84 B, with 87 A stripes. Abaxial surface: Lighter than, but closest to 76 D, flushed with 84 C, with 87 B-C stripes. Labellum: Adaxial surface: Central area white striped and speckled with 60 A. Callosities: 13 A, speckled with 60 A. Lateral lobes: 78 A, 59 B, and 178 C. Midlobe: 70 A, 59 B, and 178 C. Abaxial surface: All three segments, central areas 155 D, becoming 78 A-B, 61A. Raceme: 200 A, 187 A.

*Flowering time.*—For untreated plants as depicted in the photo on Sheet 1, which are flowering for the second time, 6–8 flowers or unopened buds are present. First flowers can be expected approximately 4–6 months after planting a 16 week old liner; approximately 3–4 flowers are present.

Floral organs: The stamens, style and stigmas are fused into a single short structure called the column, possessing one terminal anther with pollen grains united into a pollinia, which are covered by an anther cap. The stigma is located under the column behind the pollinia. Ovary inferior, three carples present.

*Column.*—The column is approximately 8.5 mm long, 6 mm wide, and 82 A in color.

*Pollinia.*—Two 1.2 mm oval masses of pollen present, 23 A in color.

*Stigma.*—Concave, sticky round 4–6 mm area under column, 155 D in color.

*Ovary.*—16 mm long, 3 mm diameter, color 84 C. Pedicel approximately 2.0 cm to 2.5 cm long, 3.5 mm in diameter, and greener than but closest to 182 D.

General appearance: Under appropriate growing conditions, plants of 'Nopsya' attain a mature size of approximately 8.0 cm to 14 cm in height and approximately 38 cm to 42 cm in width.

Leaves:

*Form.*—The leaf blade is long and elliptic to obovate with an obtuse to slightly retuse apex and a cuneate base. The margins are entire. The midrib is straight over the length of the leaf. The leaf blade is folded upward from the midrib. The leaf is often curved downward. The upper leaf surface is slightly glossy, more so on newly emerged leaves. The leaves are leathery and thick.

*Size.*—Leaf blades of a mature sized plant are approximately 18 cm to 37 cm in length and approximately 6.8 cm to 7.2 cm in width.

*Veins.*—Veins are sunken, within the thick leaf blade.

*Color.*—Adaxial surface: Darker and greener than, but closest to 137 A. Abaxial surface: 146 A, often flushed with anthocyanous 59 A.

Roots: Very thick greenish white fleshy roots.

General observation: 'Nopsya' produces long lasting flowers which are light pink with fine pink stripes, and a contrasting dark center. The inflorescence is short and easily packaged for shipping. The plant grows very quickly to marketable size. 'Nopsya' can be economically propagated via tissue culture.

It is claimed:

1. A new and distinct cultivar of Phalaenopsis orchid plant named 'Nopsya', as illustrated and described.

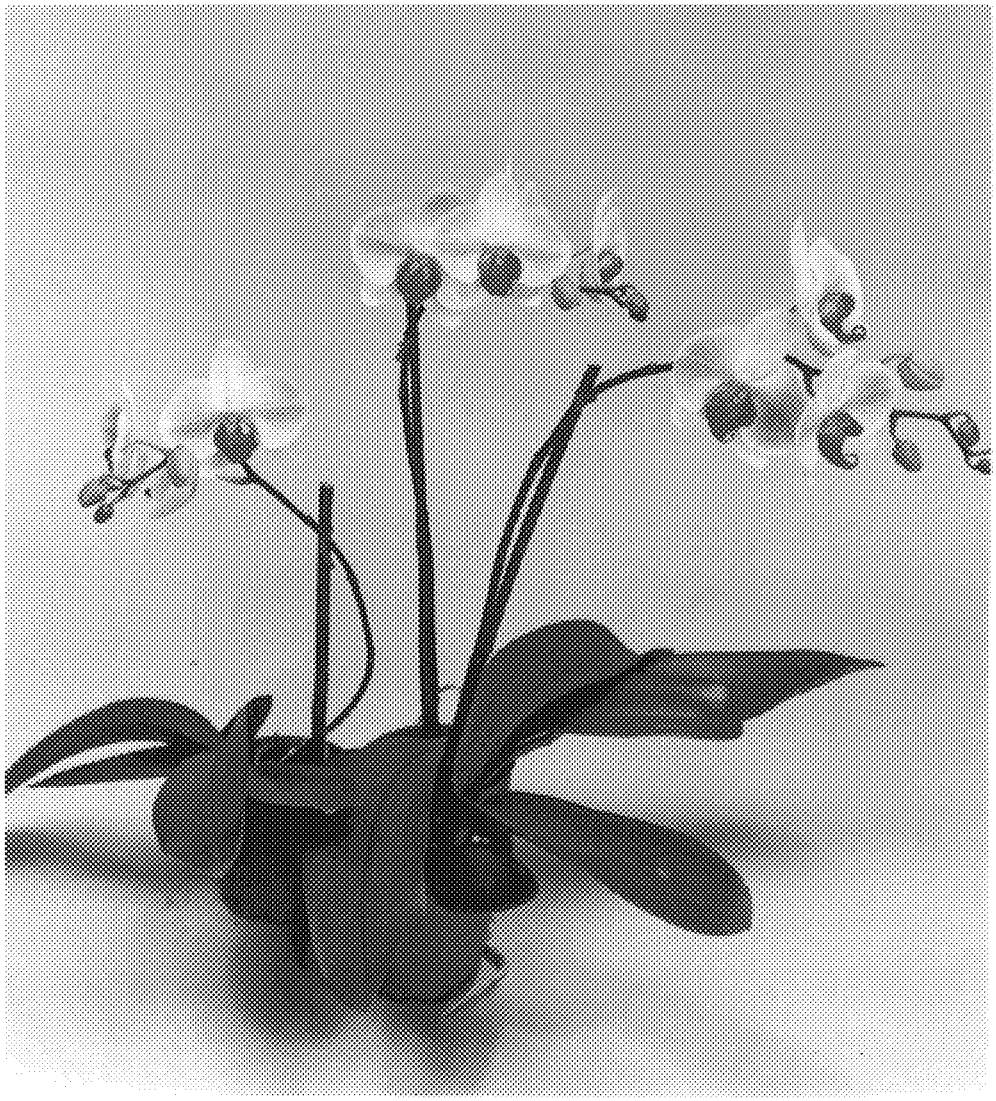

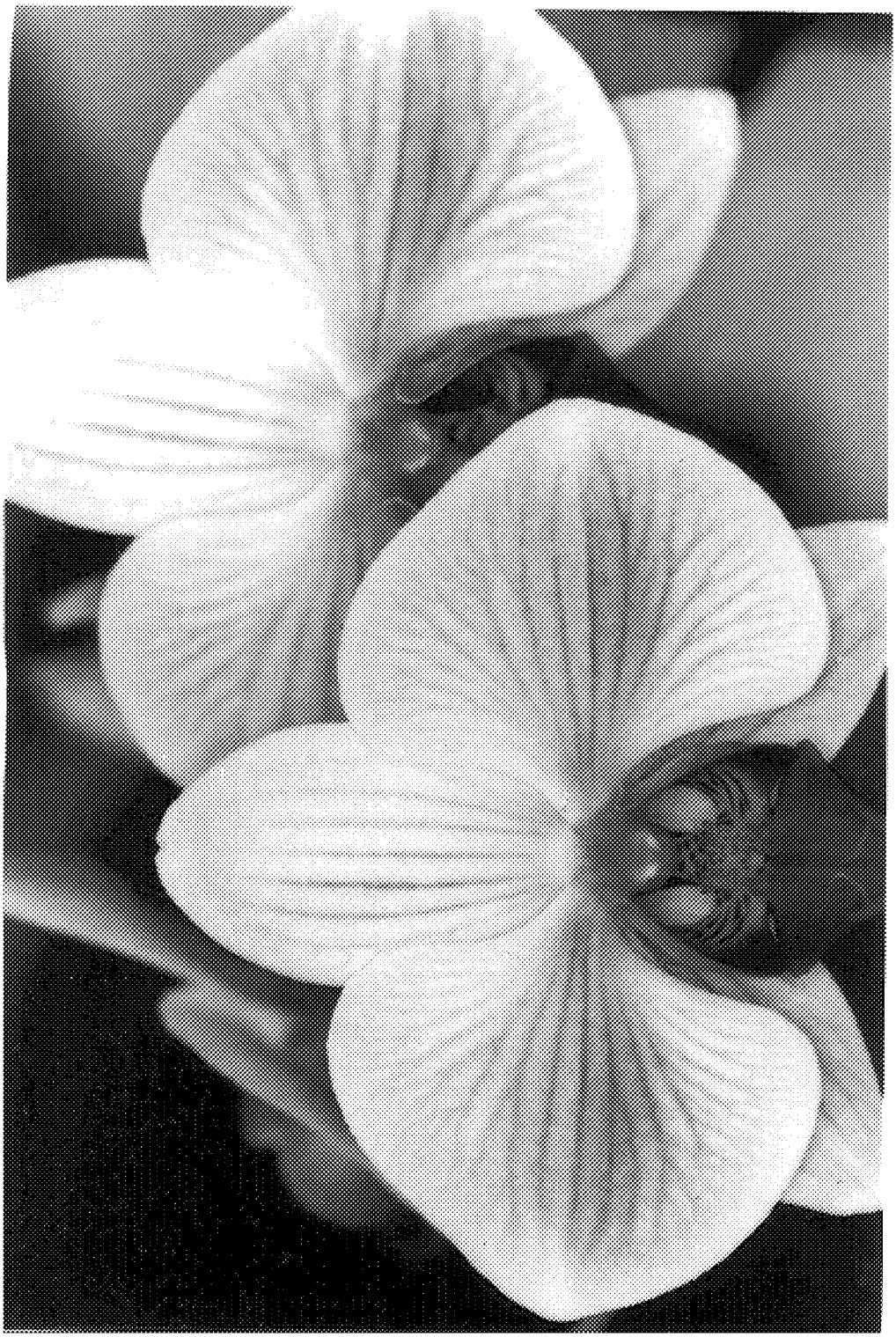

* * * * *